(12) United States Patent
Lehtinen et al.

(10) Patent No.: US 12,102,749 B2
(45) Date of Patent: Oct. 1, 2024

(54) AGENT DELIVERY SYSTEMS AND METHODS OF USING THE SAME

(71) Applicant: Boston Scientific Scimed, Inc., Maple Grove, MN (US)

(72) Inventors: Laurie Lehtinen, Boylston, MA (US); Lauren Lydecker, Millbury, MA (US); Andrew Pic, Northboro, MA (US); Gerald Fredrickson, Westford, MA (US); Ra Nam, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 880 days.

(21) Appl. No.: 17/135,571

(22) Filed: Dec. 28, 2020

(65) Prior Publication Data

US 2021/0205548 A1 Jul. 8, 2021

Related U.S. Application Data

(60) Provisional application No. 62/957,540, filed on Jan. 6, 2020.

(51) Int. Cl.
*A61M 13/00* (2006.01)
*A61M 39/22* (2006.01)

(52) U.S. Cl.
CPC ............ *A61M 13/00* (2013.01); *A61M 39/22* (2013.01); *A61M 2202/064* (2013.01); *A61M 2205/07* (2013.01)

(58) Field of Classification Search
CPC .................. A61M 31/00; A61M 39/22; A61M 2202/064; A61M 2205/07
See application file for complete search history.

(56) References Cited

U.S. PATENT DOCUMENTS

| | | | |
|---|---|---|---|
| 471,854 | A | 3/1892 | Howard |
| 881,238 | A | 3/1908 | Hasbrouck |
| 1,145,520 | A | 7/1915 | Smith |
| 1,599,959 | A | 9/1926 | Buheiji |
| 1,732,566 | A | 10/1929 | McKendrick |

(Continued)

FOREIGN PATENT DOCUMENTS

| | | |
|---|---|---|
| CN | 101401956 B | 11/2012 |
| DE | 60215438 T2 | 8/2007 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Nathan R Price
*Assistant Examiner* — Mark A Igel
(74) *Attorney, Agent, or Firm* — Bookoff McAndrews, PLLC (57) ABSTRACT

A medical device that includes an enclosure for storing an agent, an agitator positioned adjacent to or within the enclosure and configured to oscillate relative to the enclosure, and an outlet having a first end in fluid communication with the enclosure and a second end in fluid communication with a channel of a delivery tube. Oscillation of the agitator causes the agent to move toward the outlet.

20 Claims, 7 Drawing Sheets

(56) References Cited

U.S. PATENT DOCUMENTS

| | | | |
|---|---|---|---|
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 3,653,380 A * | 4/1972 | Hansen | A61M 13/00 |
| | | | 128/203.15 |
| 3,669,113 A | 6/1972 | Altounyan et al. | |
| 3,940,061 A | 2/1976 | Gimple et al. | |
| 4,184,258 A | 6/1980 | Barrington et al. | |
| 4,427,450 A | 1/1984 | Kostansek | |
| 4,457,329 A | 7/1984 | Werley et al. | |
| 4,806,167 A | 2/1989 | Raythatha | |
| 4,836,417 A * | 6/1989 | Uchiyama | B65B 37/04 |
| | | | 222/63 |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A * | 8/1995 | Terakura | A61M 13/00 |
| | | | 604/24 |
| 5,470,311 A | 11/1995 | Setterstrom et al. | |
| 5,884,621 A | 3/1999 | Matsugi et al. | |
| 5,951,531 A | 9/1999 | Ferdman et al. | |
| 6,003,512 A | 12/1999 | Gerde | |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 * | 9/2018 | Eder | A61C 3/025 |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 * | 5/2021 | Hernandez | B63C 9/24 |
| 2004/0107963 A1 | 6/2004 | Finlay et al. | |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0038027 A1 * | 2/2006 | O'Connor | B05B 7/066 |
| | | | 239/589 |
| 2006/0213514 A1 | 9/2006 | Price et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0192565 A1 * | 8/2008 | Johnson | B01F 31/265 |
| | | | 366/109 |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0305505 A1 | 12/2010 | Ducharme et al. | |
| 2011/0073200 A1 | 3/2011 | Overvaag et al. | |
| 2011/0274726 A1 | 11/2011 | Guo et al. | |
| 2011/0308516 A1 | 12/2011 | Price et al. | |
| 2013/0218072 A1 * | 8/2013 | Kubo | A61M 13/00 |
| | | | 604/58 |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 * | 7/2018 | Smith | A61M 13/00 |
| 2018/0214160 A1 | 8/2018 | Hoskins et al. | |
| 2018/0339144 A1 * | 11/2018 | Greenhalgh | A61M 35/003 |
| 2019/0134366 A1 | 5/2019 | Erez et al. | |
| 2019/0217315 A1 | 7/2019 | Maguire et al. | |
| 2019/0232030 A1 * | 8/2019 | Pic | A61B 17/00491 |
| 2021/0024187 A1 | 1/2021 | Fawcett et al. | |

(56) References Cited

U.S. PATENT DOCUMENTS

2021/0069485 A1 3/2021 Rogier
2021/0353912 A1* 11/2021 Kiev .................. A61M 25/0631

FOREIGN PATENT DOCUMENTS

| EP | 0646385 | A1 | | 4/1995 | |
|----|---------|----|----|--------|---|
| EP | 1033543 | B1 | * | 11/2007 | ............. B64G 1/402 |
| EP | 3052168 | B1 | | 11/2019 | |
| JP | H07118305 | A | | 5/1995 | |
| WO | 03013552 | A1 | | 2/2003 | |
| WO | 2004066806 | A2 | | 8/2004 | |
| WO | 2005062896 | A2 | | 7/2005 | |
| WO | 2006071649 | A2 | | 7/2006 | |
| WO | 2006088912 | A2 | | 8/2006 | |
| WO | 2008033462 | A2 | | 3/2008 | |
| WO | 2009061409 | A1 | | 5/2009 | |
| WO | 2015050814 | A1 | | 4/2015 | |
| WO | 2018157772 | A1 | | 9/2018 | |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.
Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.
Regalia, Kristen, et al. "Hemospray in Gastrointestinal Bleeding." Practical Gastroenterology. Endoscopy: Opening New Eyes, ser. 8, May 2014, pp. 13-24. 8.
Cook Medical. Hemospray Endoscopic Hemostat, Cook, 2014. (7 pages, in English).
"Hemospray Clinical Experience Shows Efficacy of a New Hemostasis Modality—v1", Cook Medical, 2012.
"Hemospray Clinical Experience Shows Efficacy of a New Hemostasis Modality—v2", Cook Medical, 2013.
"Hemospray Clinical Experience Shows Efficacy of a New Hemostasis Modality—v3", Cook Medical, 2014.
Aslanian, Harry R., and Loren Laine. "Hemostatic powder spray for GI bleeding." Gastrointestinal endoscopy 77.3 (2013): 508-510.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.
RETSCH GmbH Haan. Sieve Analysis: Taking a Close Look at Quality, An Expert Guide to Particle Size Analysis. 2015. (56 pages, in English).
Micromeritics. Density Analysis, 2001. (6 pages, in English).
Micromeritics. "Application Note: Bulk and Skeletal Density Computations for the AutoPore." May 2012. (3 pages, in English).
Arefnia, Ali, et al. "Comparative Study on the Effect of Tire-Derived Aggregate on Specific Gravity of Kaolin." Electronic Journal of Geotechnical Engineering 18 (2013): 335-44.
Kesavan, Jana, et al. "Density Measurements of Materials Used in Aerosol Studies". Edgewood Chemical Biological Center Aberdeen Proving Ground MD, 2000.
International Search Report and Written Opinion in related PCT/US2020/067175, dated Mar. 25, 2021 (English, 11 pages).

* cited by examiner

AGENT DELIVERY SYSTEMS AND METHODS OF USING THE SAME

CROSS-REFERENCE TO RELATED APPLICATIONS

This application claims the benefit of priority from U.S. Provisional Application No. 62/957,540, filed on Jan. 6, 2020, which is incorporated by reference herein in its entirety.

TECHNICAL FIELD

Various aspects of this disclosure relate generally to agent delivery systems, devices, and related methods. More specifically, at least certain embodiments of the disclosure relate to systems, devices, and related methods for metering a dose of a therapeutic agent delivered to a target treatment site, among other aspects.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered. Agent delivery may be achieved by utilizing pressurized fluid systems, for example. Such systems, however, may provide difficulties in controlling a delivery rate of the agent. Accordingly, a desired rate of agent delivery or a desired dosage of agent may not be achieved, which may result in the agent clogging portions of the delivery device, may result in inconsistent dosing of agent, or may not result in the agent reaching the treatment site deep within the GI tract. This disclosure may solve one or more of these issues or other issues in the art.

SUMMARY

Aspects of the disclosure relate to, among other things, systems, devices, and methods for metering delivery of a dose of an agent, among other aspects. Each of the aspects disclosed herein may include one or more of the features described in connection with any of the other disclosed aspects.

According to an example, a medical device includes an enclosure for storing an agent, an agitator positioned adjacent to or within the enclosure and configured to oscillate relative to the enclosure, and an outlet having a first end in fluid communication with the enclosure and a second end in fluid communication with a channel of a delivery tube. Oscillation of the agitator causes the agent to move toward the outlet.

Any of the medical devices described herein may have any of the following features. The delivery tube is in fluid communication with a pressurized medium source that stores a pressurized fluid. The delivery tube receives the pressurized fluid through the delivery tube such that the delivery tube is configured to deliver the agent received from the outlet through the delivery tube via the pressurized fluid. The enclosure is fluidly coupled to a pneumatic system via a valve, wherein the pneumatic system stores a second pressurized fluid. The valve is configured to permit delivery of the second pressurized fluid from the pneumatic system to the enclosure in response to actuation of the valve. The agitator is configured to oscillate relative to the enclosure in response to the enclosure receiving the second pressurized fluid from the pneumatic system. The agent includes a hemostatic powder. The agitator includes a diaphragm, a plunger, a piston, or an auger conveyor. The outlet includes a valve. The agitator includes a diaphragm and one or more walls that define a void, wherein at least one of the one or more walls is configured to move relative to the enclosure in response to movement of the diaphragm. The diaphragm and the at least one of the one or more walls are configured to oscillate when a pressurized medium is received within the void. Further including a coupling rod and a wheel, wherein the coupling rod has a first end coupled to the wheel and a second end coupled to the agitator. The coupling rod is configured to oscillate the agitator in response to the wheel rotating. The wheel is coupled to a motor that is operable to rotate the wheel.

According to another example, a medical device includes an enclosure for storing an agent. The medical device includes an agitator positioned adjacent to or within the enclosure. The agitator is configured to create pressure change within the enclosure via oscillation of the agitator relative to the enclosure. The medical device includes an outlet having a first end in fluid communication with the enclosure and a second end in fluid communication with a delivery tube. In response to oscillation of the agitator the agent is positioned towards the delivery tube, such that initiating a pressurized fluid propels the agent through the delivery tube.

Any of the medical devices described herein may have any of the following features. The outlet is configured to control a dose of the agent outputted from the enclosure toward the delivery tube. The agitator includes a diaphragm, one or more walls coupled to the diaphragm, and a void defined between the diaphragm and the one or more walls. The diaphragm is configured to oscillate relative to the enclosure in response to the void receiving a pressurized medium and at least one of the one or more walls moving away from the diaphragm. The agitator includes a piston that is configured to oscillate relative to the enclosure in response to the piston receiving a force that is generated by a motor.

According to another example, a method of delivering an agent to a target site via a medical device that includes an enclosure, an agitator, and a delivery tube, includes oscillating the agitator relative to the enclosure to direct the agent stored within the enclosure to the delivery tube. The agitator is oscillated in response to actuation of a first source of pressure that is in fluid communication with the enclosure. The method includes delivering the agent to the target site via the delivery tube, in response to actuation of a second source of pressure that is in fluid communication with the delivery tube.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

This disclosure is drawn to systems, devices, and methods for endoscopic delivery of, for example, a hemostatic agent, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Embodiments of this disclosure may be used to deliver a material to a target treatment site experiencing bleeding to achieve hemostasis. For example, a hemostatic agent in the form of a powder may be delivered to treat a gastrointestinal bleed by a medical device that includes an agitator that oscillates to deliver the hemostatic agent. In some embodiments, the agitator may oscillate to deliver the hemostatic agent via systems that are separate from a delivery mechanism of the medical device. Embodiments of the disclosure are not limited to such devices and methods, and instead may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various embodiments described herein include single-use or disposable medical devices.

In one exemplary embodiment a medical device for delivering the hemostatic material may include an enclosure for storing an agent and an agitator positioned adjacent to or within the enclosure, with the agitator of the medical device capable of oscillating relative to the enclosure. The medical device further includes an outlet having a first end in fluid communication with the enclosure and a second end in fluid communication with a channel of a delivery tube. The oscillation of the agitator is configured to provide movement of the agent toward the first end of the outlet and to the second end of the outlet such that the agent is received within the delivery tube. Reference will now be made in detail to examples of the disclosure described above and illustrated in the accompanying drawings. Wherever possible, the same reference numbers will be used throughout the drawings to refer to the same or like parts.

Figure 1:
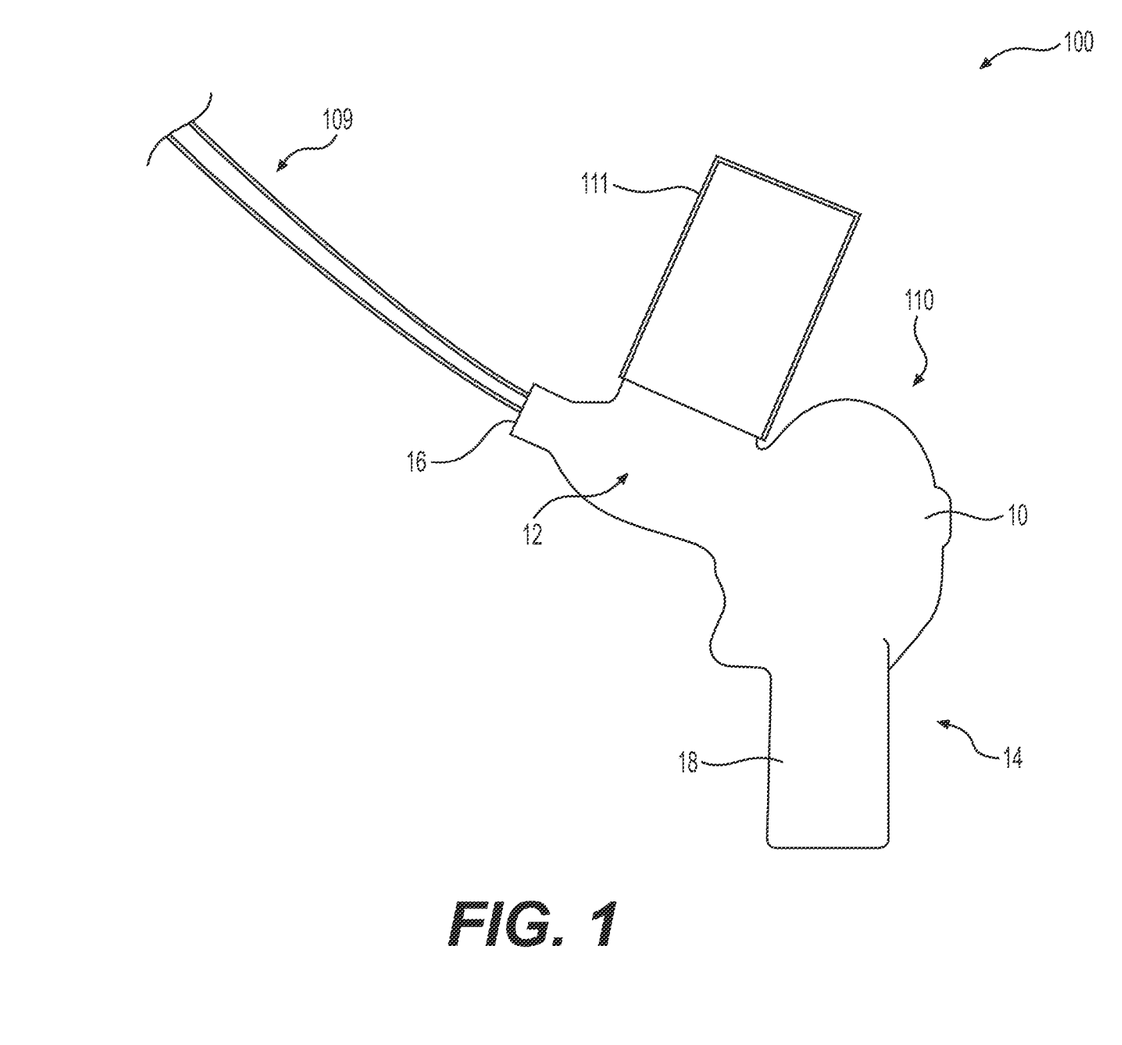
FIG. 1 is a side view of an exemplary medical system, according to aspects of this disclosure.

FIG. 1 shows a side view of an exemplary medical system 100 in accordance with an embodiment of this disclosure. The medical system 100 may include an insertion portion 109 and a proximal portion 110. The proximal portion 110 may have a body 10 defined by a distal end 12 and a proximal end 14, with the distal end 12 of the proximal portion 110 including a port 16 couple to the insertion portion 109 In some embodiments, the insertion portion 109 of the medical system 100 may include a catheter, an endoscope, a tube, etc. for delivering a material to a target treatment site within a patient. The proximal end 14 of the proximal portion 110 may include a handle 18 that is sized and shaped to be manually graspable by a user of the proximal portion 110, for example, during a procedure. It should be appreciated that a size, shape, profile and/or configuration of the insertion portion 109 and/or the proximal portion 110 shown and described herein is merely illustrative such that they may include various other suitable arrangements without departing from a scope of this disclosure.

The proximal portion 110 of the medical system 100 may further include a housing 111 that is sized and shaped to store one or more components of the proximal portion 110 therein. In the embodiment, the housing 111 is positioned adjacent to the distal end 12 of the body 10, however, it should be understood that the housing 111 may be located at various other positions along the body 10. Additionally and/or alternatively, in other embodiments the housing 111, for example, the one or more components stored within the housing 111, may be disposed within the body 10.

Figure 2A:
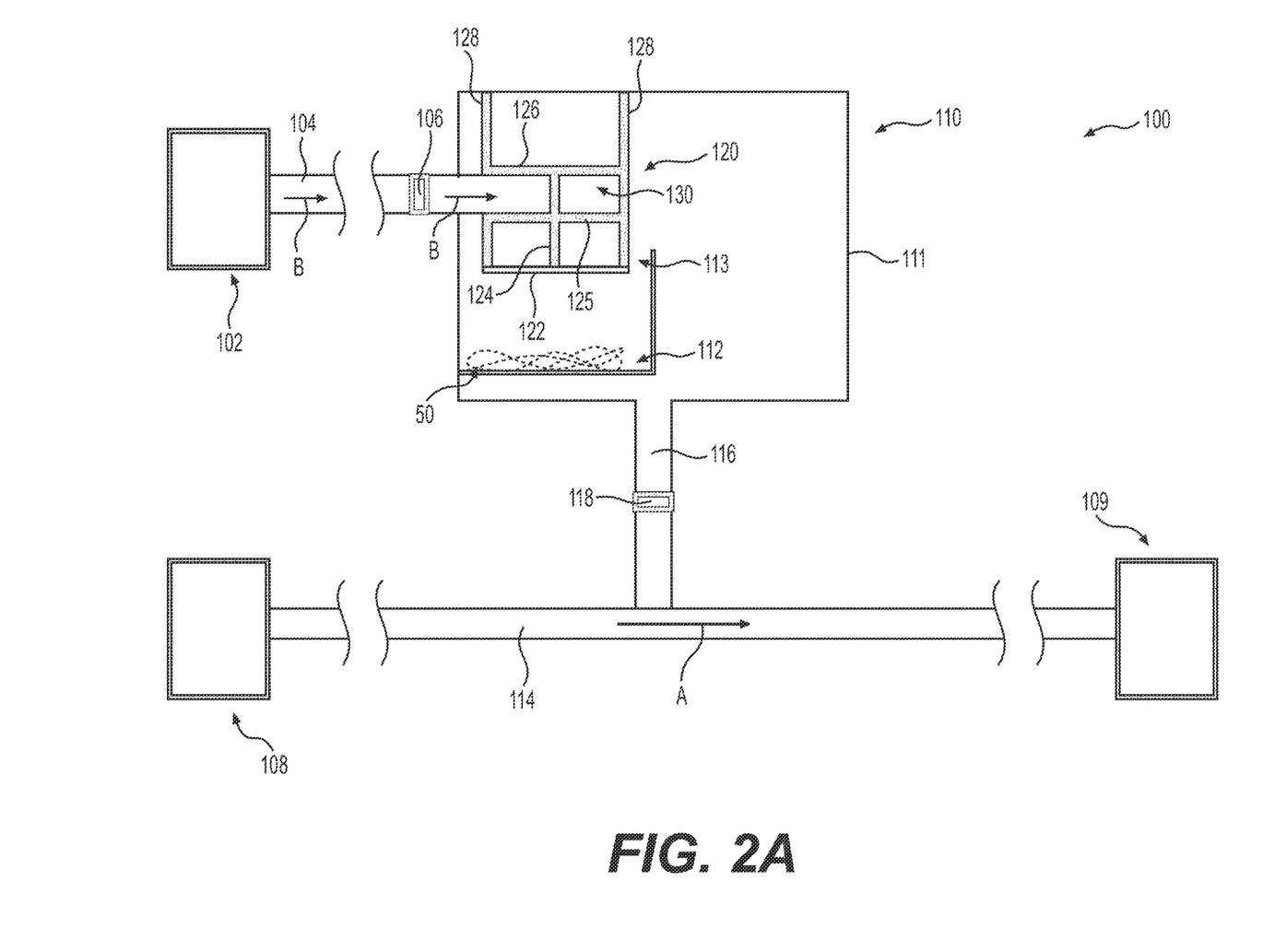
FIG. 2A is an illustrative schematic of an exemplary medical device of the medical system of FIG. 1 including an agitator in a first position, according to aspects of this disclosure.

Referring now to FIG. 2A, a schematic illustration of the medical system 100 is depicted with the insertion portion 109 and the proximal portion 110 in fluid communication with one another via one or more components of the proximal portion 110. In some embodiments, the proximal portion 110 may include a first pressurized medium source 102, a second pressurized medium source 108, and a delivery tube 114. The first pressurized medium source 102 and the second pressurized medium source 108 may each store a pressurized medium therein, such as, for example, a pressurized fluid, such as air/gas (e.g., $CO_2$). The first pressurized medium source 102 and/or the second pressurized medium source 108 may include a pneumatic system, such as, for example, a pressurized cylinder. In some embodiments, the first pressurized medium source 102 and the second pressurized medium source 108 may be disposed within the body 10 of the proximal portion 110 and, in other embodiments, may be positioned external to the body 10 of the proximal portion 110. As described in greater detail herein, the first pressurized medium source 102 may be configured to supply the housing 111 with a pressurized medium, and the second pressurized medium source 108 may be configured to supply the delivery tube 114 with a pressurized medium.

In the embodiment, the first pressurized medium source 102 is in fluid communication with the housing 111 of the proximal portion 110 via an inlet 104, such that a first end of the inlet 104 is fluidly coupled to the first pressurized medium source 102 and a second end of the inlet 104 is fluidly coupled to the housing 111. The proximal portion 110 may include a valve 106 positioned within the inlet 104 and configured to control a rate of delivery of pressurized medium from the first pressurized medium source 102 to the housing 111. In some embodiments, the valve 106 may include, for example, a relief valve, a duckbill valve, a shelf, a rotatable wheel, and/or various other suitable devices capable of controlling and/or limiting a rate of delivery of the pressurized medium from the first pressurized medium source 102 to the housing 111 via the inlet 104. For instance, the valve 106 may be electrically actuatable by a user of the proximal portion 110 to control delivery of the pressurized medium. In other embodiments, the first pressurized medium source 102 may include a pressure regulator mechanism in addition to and/or in lieu of the valve 106 for controlling and/or limiting delivery of the pressurized medium to the housing 111. By way of further example, in some embodiments the valve 106 may include an orifice having a predefined and/or adjustable size (e.g., diameter) to regulate a delivery rate of the pressurized medium.

In the embodiment, the housing 111 is in fluid communication with the delivery tube 114 via an outlet 116, such that a first end of the outlet 116 is fluidly coupled to the housing 111 and a second end of the outlet 116 is fluidly coupled to the delivery tube 114. A valve 118 is positioned within the outlet 116 and configured to control a rate of delivery of a material stored in the housing 111 (e.g., an agent 50) to the delivery tube 114. In some embodiments, the valve 118 may include for example, a relief valve, a duckbill valve, a shelf, a rotatable wheel, and/or various other suitable devices capable of controlling and/or limiting a rate of delivery of the agent 50 from the housing 111 to the delivery tube 114 via the outlet 116.

Still referring to FIG. 2A, the proximal portion 110 may include an enclosure 112 and an agitator 120 disposed within the housing 111. The enclosure 112 is positioned within the housing 111 such that the enclosure 112 at least partially partitions the housing 111. In the embodiment, the enclosure 112 defines a space within the housing 111 that is sized, shaped, and configured to store a material therein, such as, for example, the agent 50. The agent 50 may include a therapeutic substance that is operable to coagulate blood, such as, for example, a hemostatic powder. In other embodiments, the agent 50 may include various other materials and/or substances suitable for delivery. The agitator 120 is positioned within the housing 111 adjacent to the enclosure 112, and in some embodiments the agitator 120 may be at least partially positioned within the enclosure 112 such that the agitator 120 at least partially partitions the enclosure 112. The agitator 120 is positioned relative to the enclosure 112 such that an opening 113 is defined between the agitator 120 and the enclosure 112, with the opening 113 facilitating fluid communication between the space defined by the enclosure 112 and a remaining cavity of the housing 111.

In the embodiment, the agitator 120 may include a diaphragm 122, a central rod 124, a fixed floor 125, a movable ceiling 126, and a pair of sidewalls 128. The diaphragm 122 of the agitator 120 may be formed of a flexibly deformable material such that the diaphragm 122 is configured to flex in response to movement of the diaphragm 122 relative to the enclosure 112. For example, the diaphragm 122 may be at least partially formed as a silicon (Si) membrane, a low-density polyethylene (LDPE) polymer, and/or the like. As described in greater detail herein, the diaphragm 122 is configured to move relative to the enclosure 112 in response to the housing 111 receiving a pressurized medium from the first pressurized medium source 102.

The diaphragm 122 is secured to, and extends between, the pair of sidewalls 128 of the agitator 120 such that the opposing terminal ends of the diaphragm 122 are coupled to the pair of sidewalls 128. Further, the diaphragm 122 is coupled to the central rod 124 along an intermediate portion of the diaphragm 122. In the embodiment, the diaphragm 122 is coupled to a first end of the central rod 124 and the movable ceiling 126 is coupled to a second end of the central rod 124. Accordingly, the diaphragm 122 is separated from the movable ceiling 126 by a longitudinal length of the central rod 124 disposed therebetween. The agitator 120 defines a void 130 between the diaphragm 122 and the movable ceiling 126 and, as described further herein, the agitator 120 is configured to receive a pressurized medium from the first pressurized medium source 102 in the void 130.

Still referring to FIG. 2A, the movable ceiling 126 of the agitator 120 is movably coupled to the pair of sidewalls 128 such that the movable ceiling 126 is configured to move (e.g., translate) relative to the pair of sidewalls 128. In the example, the movable ceiling 126 is slidably coupled to the pair of sidewalls 128 such that the movable ceiling 126 is configured to move along a longitudinal length of the sidewalls 128. In some examples, the opposing terminal ends of the movable ceiling 126 may be configured to move symmetrically, uniformly, and/or equally relative to one another along the respective sidewalls 128. In other examples, the opposing terminal ends of the movable ceiling 126 may be configured to move asymmetrically relative to one another along the respective sidewalls 128.

With the movable ceiling 126 coupled to the central rod 124, and the central rod 124 further coupled to the diaphragm 122, the movable ceiling 126 is operable to move the central rod 124 and the diaphragm 122 in response to movement (e.g., translation) of the movable ceiling 126 relative to the pair of sidewalls 128. It should be appreciated that a size, shape, profile and/or configuration of the enclosure 112 and/or the agitator 120 shown and described herein is merely illustrative such that the enclosure 112 and/or the agitator 120 may include various other suitable arrangements without departing from a scope of this disclosure.

Still referring to FIG. 2A, the fixed floor 125 of the agitator 120 may be fixed relative to the diaphragm 122, the central rod 124, and the movable ceiling 126. In the example, the fixed floor 125 extends between the pair of sidewalls 128 and is positioned between the diaphragm 122 and the movable ceiling 126. Further, the fixed floor 125 may be oriented relatively parallel to the diaphragm 122 and the movable ceiling 126, and transverse to the central rod 124. In some examples, the central rod 124 may extend through the fixed floor 125, such as, for example, through an aperture formed in the fixed floor 125 (not shown). In other examples, the central rod 124 may extend adjacently to the fixed floor 125.

As described in further detail herein, the fixed floor 125 is configured to engage the diaphragm 122 of the agitator 120 as the central rod 124 and the movable ceiling 126 move relative to the pair of sidewalls 128 (e.g., in an upward direction). In this instance, the fixed floor 125 is operable to form an impediment for a further translation of the central rod 124 and/or deformation of the diaphragm 122 beyond a predetermined extent relative to the enclosure 112 and/or the pair of sidewalls 128. It should be understood that, in other embodiments, the fixed floor 125 of the agitator 120 may be omitted entirely such that the central rod 124 and/or the diaphragm 122 may translate and deform to various other suitable extents than those shown and described herein, respectively.

According to an example method of using the medical system 100, the agent 50 may be initially stored in the enclosure 112 of the housing 111 and the insertion portion 109 may be fluidly coupled to the delivery tube 114 of the proximal portion 110 (e.g., at the port 16 of the body 10). In this instance, upon activation of the first pressurized medium source 102, a pressurized medium may be transmitted to the housing 111 via the inlet 104. The pressurized medium may be delivered in a direction B through the inlet 104 and into the housing 111 via the valve 106. The agitator 120 may receive the pressurized medium within the void 130, thereby causing the movable ceiling 126 to move relative to the pair of sidewalls 128 in response. For example, the movable ceiling 126 may move away from the diaphragm 122 as the void 130 receives the pressurized medium therein such that the central rod 124 moves (e.g., translates) simultaneously with the movable ceiling 126. With the central rod 124 coupled to the diaphragm 122, the diaphragm 122 is configured to move relative to the enclosure 112 and toward the movable ceiling 126.

Figure 2B:
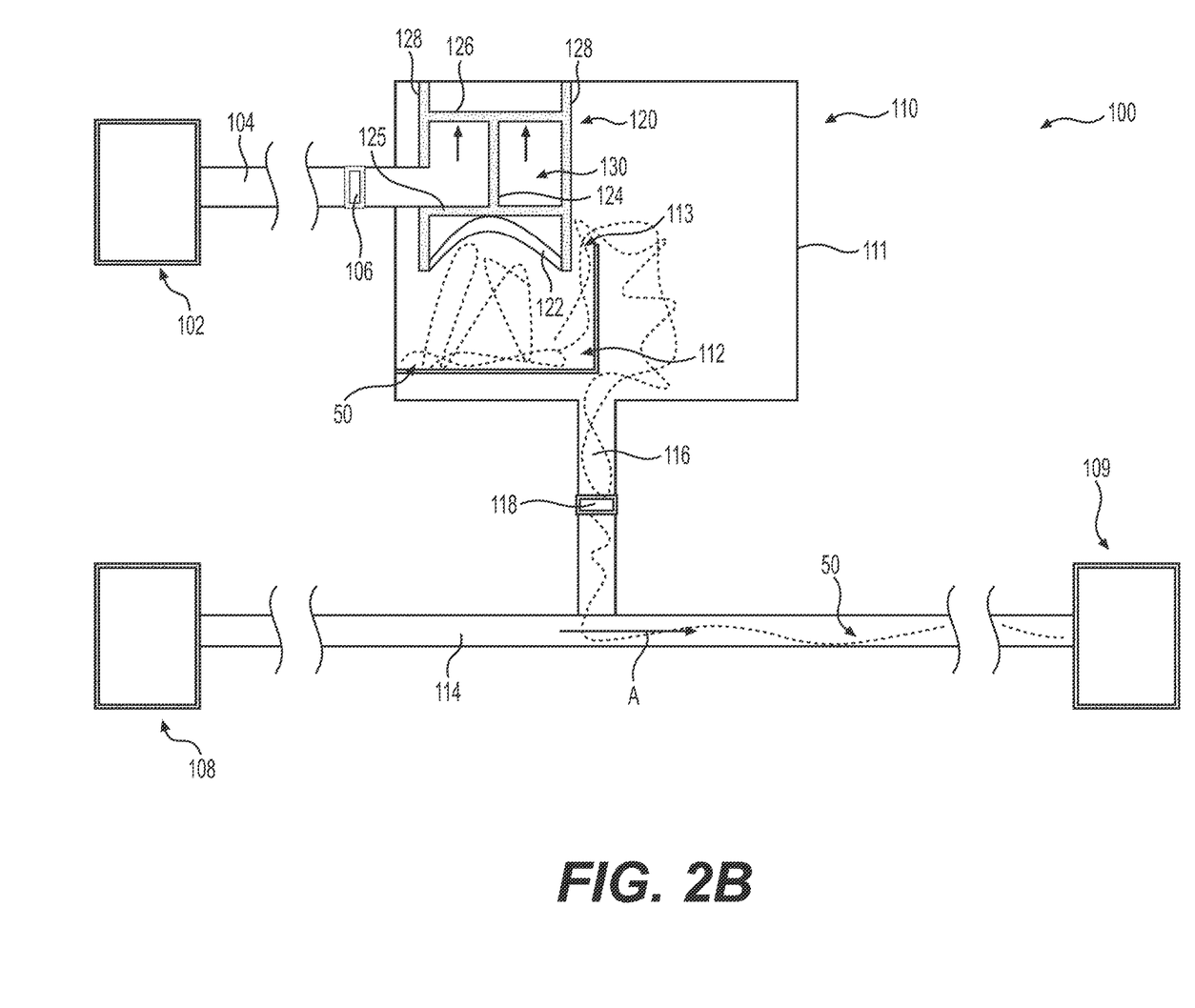
FIG. 2B is an illustrative schematic of the medical device of FIG. 2A with the agitator oscillating to a second position, according to aspects of this disclosure.

Referring now to FIG. 2B, the diaphragm 122, the central rod 124, and the movable ceiling 126 of the agitator 120 are depicted in a second, actuated position in response to the void 130 receiving the pressurized medium therein. Accordingly, the diaphragm 122 is configured to flexibly deform in response to the movable ceiling 126 moving relative to the enclosure 112 due to the diaphragm 122 being secured to the pair of sidewalls 128 at the opposing terminal ends of the diaphragm 122 and coupled to the central rod 124 along an intermediate portion of the diaphragm 122. The central rod 124 pulls and/or pushes the diaphragm 122 in a direction of movement of the movable ceiling 126 until the diaphragm 122 and/or the central rod 124 engages the fixed floor 125 of the agitator 120. In this instance, the fixed floor 125 serves as an impediment for further translation of the central rod 124 and/or deformation of the diaphragm 122 beyond a predetermined extent relative to the enclosure 112 and/or the pair of sidewalls 128. It should be understood that, in other embodiments, the fixed floor 125 of the agitator 120 may be omitted entirely such that the central rod 124 and/or the diaphragm 122 may translate and deform to various other suitable extents than those shown and descried herein, respectively.

In the embodiment, movement of the diaphragm 122 of the agitator 120 creates a pressure change within the enclosure 112 of the housing 111, thereby causing the agent 50 stored within the enclosure 112 to move. The diaphragm 122 is configured to oscillate relative to the enclosure 112 in response to the first pressurized medium source 102 delivering the pressurize medium to the housing 111 via the inlet 104 and the valve 106 controlling and/or limiting a rate of delivery of the pressurized medium. Accordingly, the diaphragm 122 of the agitator 120 may repeatedly oscillate relative to the enclosure 112 to a plurality of positions relative to an initial position (see FIG. 2A) and an actuated position (see FIG. 2B). In response to the pressure change generated within the enclosure 112 by the agitator 120 (e.g., a pressure drop followed by an increase in pressure), the agent 50 is agitated (e.g., moved) within the enclosure 112 toward the outlet 116 of the proximal portion 110 via the opening 113. In other words, an oscillation of the agitator 120 may cause movement of the agent 50 from the enclosure 112 toward the outlet 116. It should be appreciated that gravitational forces within the enclosure 112 of the housing 111 may further facilitate movement of the agent 50 toward the outlet 116, such as, for example, between oscillations of the agitator 120. In examples where the agent 50 includes a hemostatic powder, the agitator 120 may be configured to at least temporarily suspend the particulate of the agent 50 in air within the enclosure 112 due to an oscillation of the agitator 120.

Still referring to FIG. 2B, the agent 50 may be received at the delivery tube 114 via the outlet 116. With the delivery tube 114 fluidly coupled to the second pressurized medium source 108 at a first end of the delivery tube 114, and to the insertion portion 109 at a second end of the delivery tube 114, the agent 50 may be delivered through the delivery tube 114 and to the insertion portion 109 via the pressurized medium passing through the delivery tube 114 in a direction A. In this instance, the pressurized medium may fluidize the agent 50 (e.g., the hemostatic powder) thereby causing the agent 50 to flow through the delivery tube 114 in a manner similar to that of a liquid. In other words, the pressurized medium (gas or liquid) may pass through and/or about the particulate of the hemostatic powder thereby moving the agent 50 fluidly and/or freely through the delivery tube 114 with minimal constraint. It should be appreciated that a rate of delivery of the agent 50 to the delivery tube 114 may be controlled and/or limited by the valve 118 in the outlet 116. Accordingly, a dose of the agent 50 received by the insertion portion 109 from the delivery tube 114 may be metered by the proximal portion 110 when delivering the agent 50 to a patient.

Additionally and/or alternatively, a dose of the agent 50 received by the insertion portion 109 may be metered by controlling an activation of the first pressurized medium source 102. As noted above, in some embodiments the first pressurized medium source 102 may include a pressure regulator mechanism for controlling and/or limiting delivery of the pressurized medium to the housing 111. The pressure regulator mechanism of the first pressurized medium source 102 may, for example, automatically activate and deactivate the first pressurized medium source 102 to selectively deliver the first pressurized medium to the housing 111 to cause an oscillation of the agitator 120. In this instance, initiating and stopping the first pressurized medium source 102 may provide a controlled delivery of the pressurized medium source thereby resulting in an alternating increase and decrease of pressure within the housing 111 and the enclosure 112 where the agitator 120 is positioned.

Figure 3A:
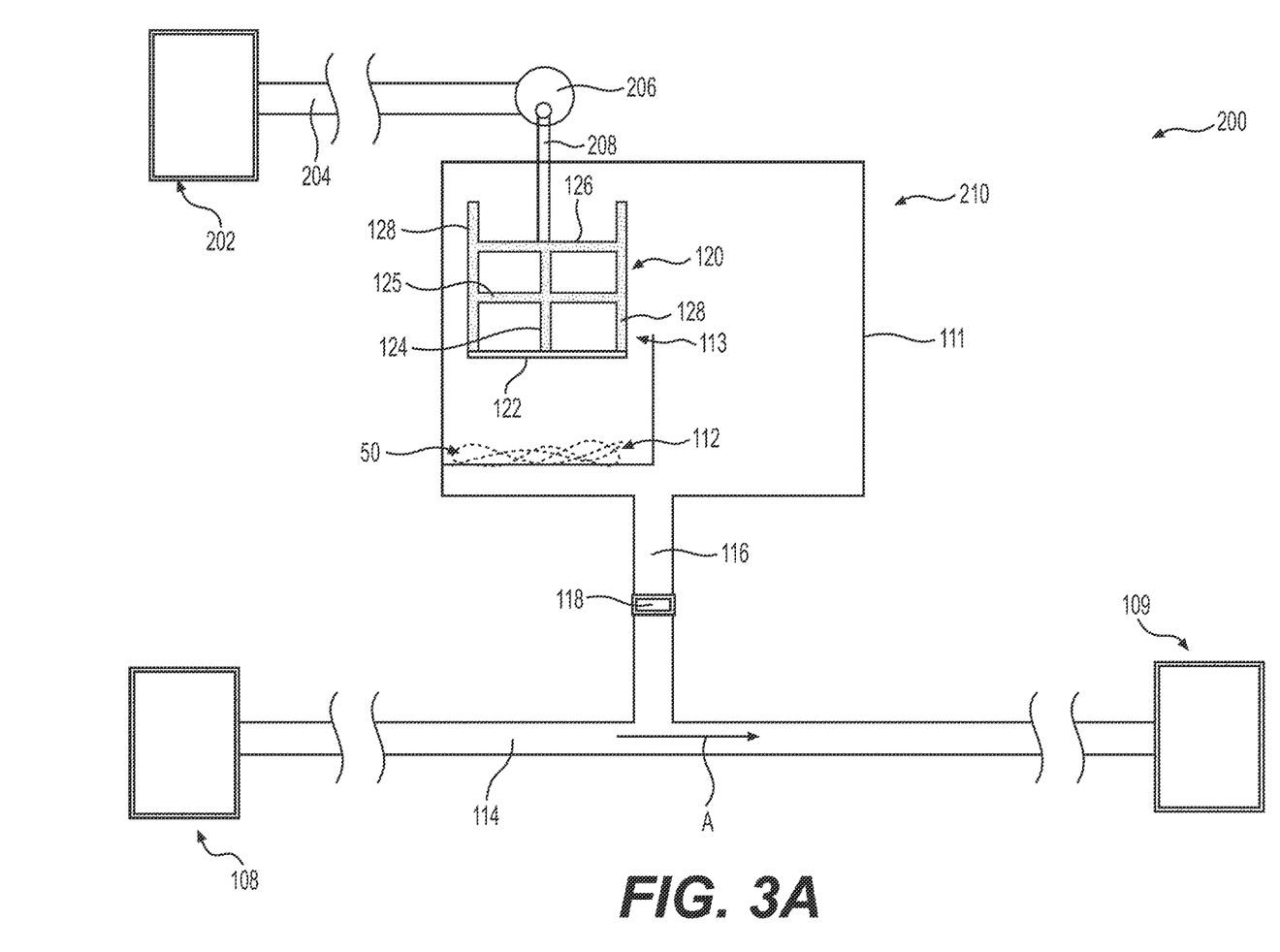
FIG. 3A is an illustrative schematic of an exemplary medical device of the medical system of FIG. 1 including an agitator in a first position, according to aspects of this disclosure.
Figure 3B:
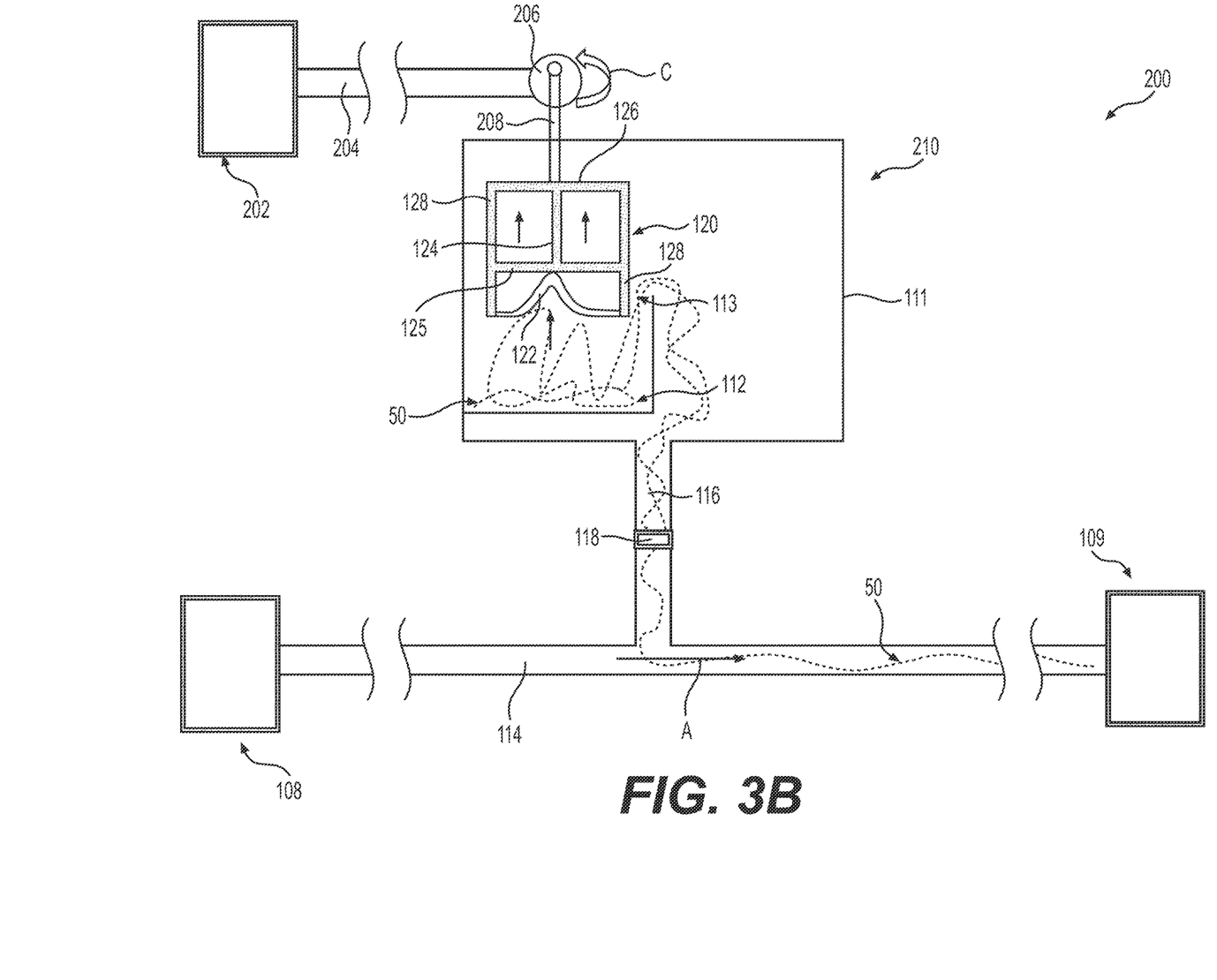
FIG. 3B is an illustrative schematic of the medical device of FIG. 3A with the agitator oscillating to a second position, according to aspects of this disclosure.

Referring now to FIGS. 3A-3B, an exemplary medical system 200 including a proximal portion 210 is depicted in accordance with an embodiment of this disclosure. Except as otherwise described below, the medical system 200 and the proximal portion 210 may be substantially similar to the medical system 100 and the proximal portion 110 described above, respectively, such that like reference numerals are used to identify like components. Accordingly, it should be understood that the medical system 200 and the proximal portion 210 may be configured and operable like the medical system 100 and the proximal portion 110, respectively, except for the differences explicitly noted herein. For example, the proximal portion 210 may include a motor 202, a wheel 206, and an agitator 120. The motor 202 is coupled to the wheel 206 via a cable or rod 204 such that actuation of the motor 202 is communicated to the wheel 206 via the rod 204. The wheel 206 is configured to rotate in response to actuation of the motor 202 and, as described in greater detail herein, cause oscillation of the agitator 120 in response.

In the embodiment, the movable ceiling 126 of the agitator 120 is coupled to the wheel 206 via a coupling rod 208 such that rotation of the wheel 206 may provide movement of the movable ceiling 126 relative to the enclosure 112 and/or the pair of sidewalls 128. For example, the proximal portion 210 may be configured such that rotation of the wheel 206 provides a translation of the movable ceiling 126 of the agitator 120. With the movable ceiling 126 coupled to the central rod 124, and the central rod 124 further coupled to the diaphragm 122, movement (e.g., translation) of the movable ceiling 126 may cause simultaneous movement (e.g., translation) of the central rod 124 and/or deformation of the diaphragm 122 relative to the enclosure 112. It should be understood that, in some embodiments, the motor 202, the rod 204, and/or the wheel 206 is disposed within the body 10 of the proximal portion 210 and, in other embodiments, may be positioned external to the body 10 of the proximal portion 210.

According to an example method of using the medical system 200, the agent 50 may be initially stored in the enclosure 112 of the housing 111 and the insertion portion 109 may be fluidly coupled to the delivery tube 114 of the proximal portion 210 (e.g., at the port 16 of the body 10). In this instance, upon activation of the motor 202, the wheel 206 may be rotated, such as, for example, in a clockwise and/or counterclockwise direction relative to the housing 111 and/or the enclosure 112. Rotation of the wheel 206 may transmit an oscillating force onto the agitator 120 (e.g., a pulling-force, a pushing-force, etc.), for example, onto the movable ceiling 126, such that the movable ceiling 126 moves relative to the pair of sidewalls 128 in response. For example, the movable ceiling 126 may move away from the diaphragm 122 as the wheel 206 rotates such that the central rod 124 moves (e.g., translates) simultaneously with the movable ceiling 126. With the central rod 124 coupled to the diaphragm 122, the diaphragm 122 is configured to move relative to the enclosure 112 and toward the movable ceiling 126.

Referring now to FIG. 3B, the diaphragm 122, the central rod 124, and the movable ceiling 126 of the agitator 120 are depicted in a second, actuated position in response to the wheel 206 rotating in a direction C. Accordingly, the diaphragm 122 is configured to flexibly deform in response to the movable ceiling 126 moving relative to the enclosure 112 due to the diaphragm 122 being secured to the pair of sidewalls 128 at the opposing terminal ends of the diaphragm 122, and coupled to the central rod 124 along an intermediate portion of the diaphragm 122. The central rod 124 pulls and/or pushes the diaphragm 122 in a direction of movement of the movable ceiling 126 until the diaphragm 122 and/or the central rod 124 engages the fixed floor 125 of the agitator 120. In this instance, the fixed floor 125 serves as an impediment for further translation of the central rod 124 and/or deformation of the diaphragm 122 beyond a predetermined extent relative to the enclosure 112, however, it should be understood that in other embodiments the fixed floor 125 may be omitted entirely.

Figure 4A:
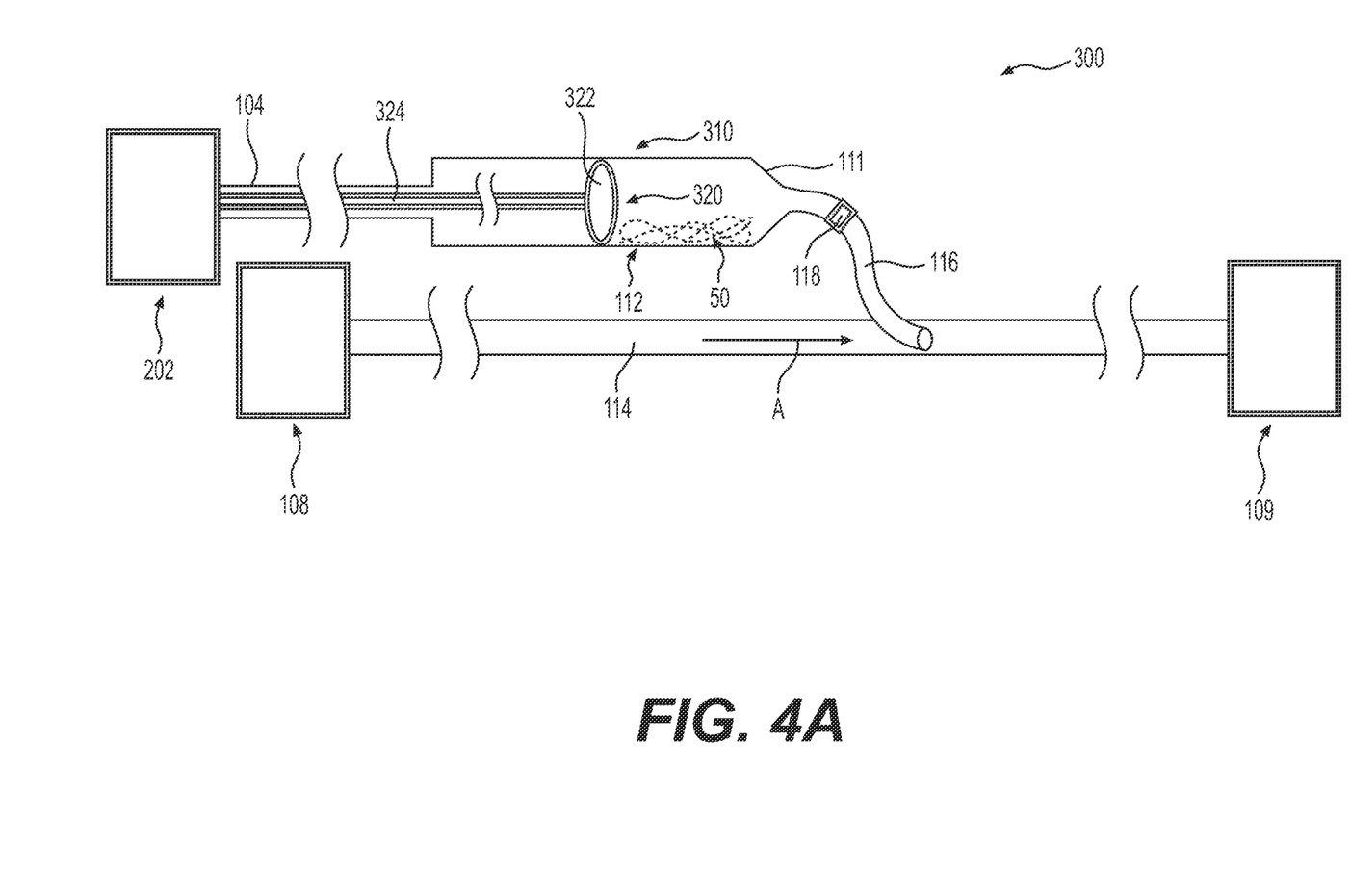
FIG. 4A is an illustrative schematic of an exemplary medical device of the medical system of FIG. 1 including an agitator in a first position, according to aspects of this disclosure.

In the embodiment, movement of the diaphragm 122 of the agitator 120 creates a pressure change within the enclosure 112 that causes the agent 50 stored within the enclosure 112 to move. The diaphragm 122 is configured to oscillate relative to the enclosure 112 in response to the motor 202 causing rotation of the wheel 206. Accordingly, the diaphragm 122 of the agitator 120 may repeatedly oscillate relative to the enclosure 112 to a plurality of positions relative to an initial position (see FIG. 3A) and an actuated position (see FIG. 3B). In response to the pressure change generated within the enclosure 112 by the agitator 120 (e.g., repeated sequences of decreasing and increasing pressure), the agent 50 is agitated (e.g., moved) within the enclosure 112 toward the outlet 116 of the proximal portion 210 via the opening 113.

Still referring to FIG. 3B, the agent 50 may be received at the delivery tube 114 via the outlet 116. With the delivery tube 114 fluidly coupled to the second pressurized medium source 108 at a first end of the delivery tube 114, and to the insertion portion 109 at a second end of the delivery tube 114, the agent 50 may be delivered through the delivery tube 114 and to the insertion portion 109 via a pressurized medium passing through the delivery tube 114 in the direction A. It should be appreciated that a rate of delivery of the agent 50 to the delivery tube 114 may be controlled and/or limited by the valve 118 in the outlet 116. Accordingly, a dose of the agent 50 received by the insertion portion 109 from the delivery tube 114 may be metered by the proximal portion 210 when delivering the agent 50 to a patient.

Referring now to FIGS. 4A-4B, an exemplary medical system 300 including a proximal portion 310 is depicted in accordance with an embodiment of this disclosure. Except as otherwise described below, the medical system 300 and the proximal portion 310 may be substantially similar to the medical system 100, 200 and the proximal portion 110, 210 described above, respectively, such that like reference numerals are used to identify like components. Accordingly, it should be understood that the medical system 300 and the proximal portion 310 may be configured and operable like the medical system 100, 200 and the proximal portion 110, 210, respectively, except for the differences explicitly noted herein. For example, the proximal portion 310 may include the delivery tube 114, the motor 202, and an agitator 320. The agitator 320 is disposed within the housing 111 of the proximal portion 310 and positioned adjacent to and/or at least partially within the enclosure 112.

In the embodiment, the agitator 320 may include a piston, a plunger, an auger conveyor, and/or any other like structure. For example, the agitator 320 may include a crown 322 and a rod shaft 324. The motor 202 is coupled to the agitator 320 via the inlet 104, for example, the motor 202 is coupled to the rod shaft 324 which extends through the inlet 104. The crown 322 of the agitator 320 is positioned at a distal end of the rod shaft 324 opposite of a proximal end of the rod shaft 324 that is coupled to the motor 202. Accordingly, actuation of the motor 202 is communicated to the crown 322 of the agitator 320 via the rod shaft 324. The rod shaft 324 is configured to move in response to actuation of the motor 202 and, as described in greater detail herein, cause oscillation of the crown 322 of the agitator 320 in response. For example, the proximal portion 310 may be configured such that translation of the rod shaft 324 relative to the inlet 104 provides a translation of the crown 322 of relative to the enclosure 112 and/or the housing 111. It should be understood that, in some embodiments, the motor 202 is disposed within the body 10 of the proximal portion 310 and, in other embodiments, may be positioned external to the body 10 of the proximal portion 310.

According to an example method of using the medical system 300, the agent 50 may be initially stored in the enclosure 112 of the housing 111 and the insertion portion 109 may be fluidly coupled to the delivery tube 114 of the proximal portion 310 (e.g., at the port 16 of the body 10). In this instance, upon activation of the motor 202, the rod shaft 324 of the agitator 320 may be moved relative to the housing 111 and/or the enclosure 112. Translation of the rod shaft 324 may transmit a force onto the crown 322 of the agitator 320 (e.g., a pulling-force, a pushing-force, etc.), such that the crown 322 moves relative to the enclosure 112 in response. It should be appreciated that, in other embodiments, the medical system 300 may include the first pressurized medium source 102 in lieu of the motor 202 for actuating the agitator 320 of the proximal portion 310.

Figure 4B:
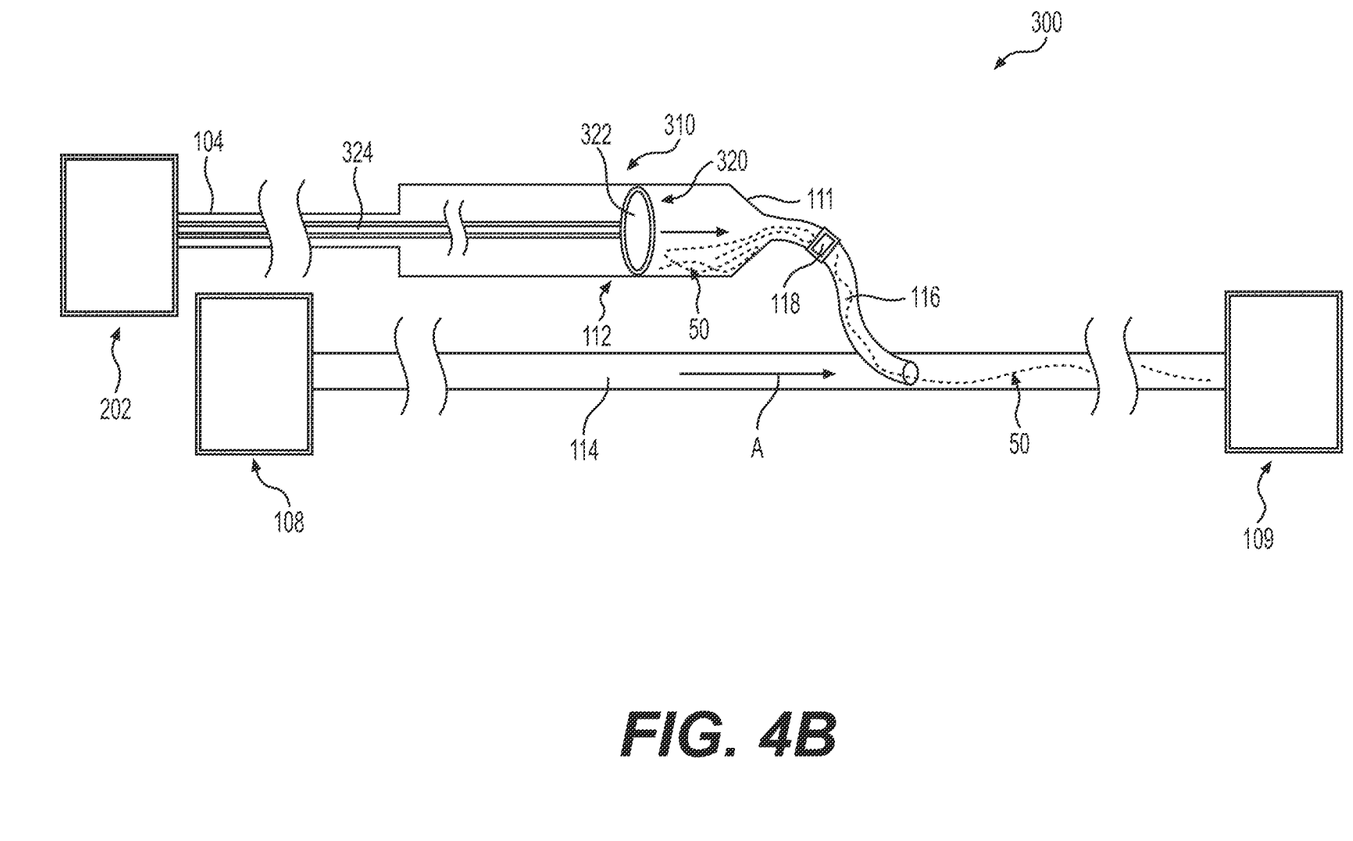
FIG. 4B is an illustrative schematic of the medical device of FIG. 4A with the agitator oscillating to a second position, according to aspects of this disclosure.

Referring now to FIG. 4B, the agitator 320 is depicted in a second, actuated position in response to the motor 202 being actuated to move the rod shaft 324. Accordingly, the crown 322 is configured to translate in response to the rod shaft 324, relative to the enclosure 112 due to the crown 322 being secured to the rod shaft 324. The rod shaft 324 pushes and/or pulls the crown 322 in a direction of movement of the rod shaft 324. In the embodiment, movement of the crown 322 of the agitator 320 creates a pressure change within the enclosure 112 that causes the agent 50 stored within the enclosure 112 to move. The crown 322 is configured to oscillate relative to the enclosure 112 in response to the motor 202 causing movement of the rod shaft 324. Accordingly, the crown 322 of the agitator 320 may repeatedly oscillate relative to the enclosure 112 to a plurality of positions relative to an initial position (see FIG. 4A) and an actuated position (see FIG. 4B). In response to the pressure change generated within the enclosure 112 by the agitator 320, the agent 50 is agitated (e.g., moved) within the enclosure 112 toward the outlet 116 of the proximal portion 310.

Still referring to FIG. 4B, the agent 50 may be received at the delivery tube 114 via the outlet 116. With the delivery tube 114 fluidly coupled to the second pressurized medium source 108 at a first end of the delivery tube 114, and to the insertion portion 109 at a second end of the delivery tube 114, the agent 50 may be delivered through the delivery tube 114 and to the insertion portion 109 via a pressurized medium passing through the delivery tube 114 in the direction A. It should be appreciated that a rate of delivery of the agent 50 to the delivery tube 114 may be controlled and/or limited by the valve 118 in the outlet 116. Accordingly, a dose of the agent 50 received by the insertion portion 109 from the delivery tube 114 may be metered by the proximal portion 310 when delivering the agent 50 to a patient. Additionally and/or alternatively, as described in detail above with respect to the medical systems 100, 200, a rate of delivering the agent 50 may increase and/or decrease in response to a rate of oscillation of the agitator 320. In the embodiment, oscillation of the agitator 320 may be controlled by repeatedly initiating and ceasing activation of the motor 202, alternating between increasing and/or decreasing a speed of the motor 202, etc.

Each of the aforementioned devices, assemblies, and methods may be used to provide controlled delivery of, for example, a hemostatic agent to a target treatment site. Any of the medical systems 100, 200, 300, for example, the insertion portions 109 of the medical systems 100, 200, 300 shown and described above, may be inserted into an endoscope, or like device, with imaging systems, lighting systems, etc., to assist in positioning the medical systems 100, 200, 300. By providing a surgical assembly that allows a user to interact with a patient's tissue experiencing a bleed using an agitator during a procedure, a user may reduce overall procedure time, increase efficiency of procedures, and avoid unnecessary harm to a patient's body caused by limited access to target tissue of a patient and/or ineffectiveness in coagulating the bleed.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device comprising:

an enclosure for storing an agent, the enclosure having an inlet and an outlet;

an agitator positioned within the enclosure between the inlet and the outlet, the agitator includes a diaphragm that is flexibly deformable and configured to oscillate between the inlet and the outlet of the enclosure; and wherein the outlet includes a first end in fluid communication with the enclosure and a second end in fluid communication with a channel of a delivery tube;

wherein oscillation of the agitator below the inlet and above the outlet causes the agent to move away from the inlet and toward the outlet.

2. The medical device of claim 1, wherein the enclosure is in fluid communication with a first pressure medium source via the inlet, wherein the first pressure medium source stores a first pressurized fluid, and the delivery tube is in fluid communication with a second pressurized medium source that stores a second pressurized fluid.

3. The medical device of claim 2, wherein the enclosure receives the first pressurized fluid through the inlet such that the diaphragm is configured to oscillate in response to the enclosure receiving the first pressurized fluid at the inlet above the diaphragm; and wherein the delivery tube receives the second pressurized fluid through the delivery tube such that the delivery tube is configured to deliver the agent received from the outlet through the delivery tube via the second pressurized fluid.

4. The medical device of claim 1, wherein the enclosure is fluidly coupled to the first pressure medium source via a valve.

5. The medical device of claim 4, wherein the valve is configured to permit delivery of the first pressurized fluid from the first pressure medium source to the enclosure in response to actuation of the valve.

6. The medical device of claim 5, wherein the agitator is configured to oscillate relative to the enclosure in response to the enclosure receiving the first pressurized fluid from the first pressure medium source.

7. The medical device of claim 1, wherein the agent includes a hemostatic powder.

8. The medical device of claim 1, wherein the diaphragm is configured to flex between a plurality of positions when oscillating between the inlet and the outlet.

9. The medical device of claim 1, wherein the outlet includes a valve.

10. The medical device of claim 1, wherein the agitator includes the diaphragm and one or more walls that define a void, wherein at least one of the one or more walls is configured to move relative to the enclosure in response to movement of the diaphragm.

11. The medical device of claim 10, wherein the diaphragm and the at least one of the one or more walls are configured to oscillate when the first pressurized fluid from the first pressurized medium source is received within the void via the inlet.

12. The medical device of claim 1, further comprising a coupling rod and a wheel, wherein the coupling rod has a first end coupled to the wheel and a second end coupled to the agitator.

13. The medical device of claim 12, wherein the coupling rod is configured to oscillate the agitator in response to the wheel rotating.

14. The medical device of claim 13, wherein the wheel is coupled to a motor that is operable to rotate the wheel.

15. A medical device comprising:
    an enclosure having an inlet and an outlet, the enclosure configured for storing an agent below the inlet and above the outlet; and
    an agitator positioned within the enclosure below the inlet and above the outlet, wherein the agitator includes a diaphragm that is flexibly deformable and configured to create pressure change within the enclosure via oscillation of the agitator between the inlet and the outlet of the enclosure;
    wherein the outlet includes a first end in fluid communication with the enclosure and a second end in fluid communication with a delivery tube; and
    wherein in response to oscillation of the agitator between the inlet and the outlet, the agent is moved away from the inlet and towards the outlet for receipt in the delivery tube, such that initiating a pressurized fluid propels the agent through the delivery tube.

16. The medical device of claim 15, wherein the outlet is configured to control a dose of the agent outputted from the enclosure toward the delivery tube.

17. The medical device of claim 16, wherein the agitator includes the diaphragm, one or more walls coupled to the diaphragm, and a void defined between the diaphragm and the one or more walls.

18. The medical device of claim 17, wherein the diaphragm is configured to oscillate relative to the enclosure in response to the void receiving a pressurized medium and at least one of the one or more walls moving away from the diaphragm.

19. A method of delivering an agent to a target site via a medical device that includes an enclosure, an agitator, and a delivery tube, the method comprising:

delivering a first pressurized fluid into the enclosure via an inlet in response to actuating a first source of pressure, wherein the agitator is positioned within the enclosure relatively below the inlet such that the first pressurized fluid enters the enclosure above the agitator;

oscillating the agitator repeatedly between a plurality of positions relative to the enclosure to direct the agent stored within the enclosure away from the inlet and to an outlet of the enclosure that is in fluid communication with the delivery tube, wherein the agitator is positioned within the enclosure relatively above the outlet and oscillated in response to actuation of the first source of pressure that is in fluid communication with the enclosure; and delivering the agent to the target site via the delivery tube with a second pressurized fluid entering the delivery tube, in response to actuation of a second source of pressure that is in fluid communication with the delivery tube.

20. The method of claim 19, wherein the agitator includes a flexibly deformable diaphragm configured to flex upon the enclosure receiving the first pressurized fluid via the inlet.

* * * * *